United States Patent
Ogata et al.

(10) Patent No.: US 8,694,078 B2
(45) Date of Patent: Apr. 8, 2014

(54) METHOD AND DEVICE FOR INSERTING ELECTRICAL LEADS

(75) Inventors: Wayne Ogata, San Ramon, CA (US); Mutsuo Nakayama, Hamada (JP)

(73) Assignee: Freedom Medi-Tech Ventures LLC, San Ramon, CA (US)

( * ) Notice: Subject to any disclaimer, the term of this patent is extended or adjusted under 35 U.S.C. 154(b) by 453 days.

(21) Appl. No.: 12/553,842

(22) Filed: Sep. 3, 2009

(65) Prior Publication Data

US 2010/0056911 A1 Mar. 4, 2010

Related U.S. Application Data

(60) Provisional application No. 61/094,374, filed on Sep. 4, 2008.

(51) Int. Cl.
*A61M 5/00* (2006.01)

(52) U.S. Cl.
USPC ............ 600/435; 604/509; 606/194; 607/116

(58) Field of Classification Search
USPC ................. 600/424, 425, 431, 433, 434, 435; 604/508, 509, 510
See application file for complete search history.

(56) References Cited

U.S. PATENT DOCUMENTS

| | | | | |
|---|---|---|---|---|
| 4,243,050 | A | * | 1/1981 | Littleford ...................... 607/122 |
| 5,160,321 | A | * | 11/1992 | Sahota ...................... 604/101.03 |
| 5,441,516 | A | * | 8/1995 | Wang et al. ................... 606/198 |
| 5,800,496 | A | * | 9/1998 | Swoyer et al. ................ 607/122 |
| 6,562,049 | B1 | * | 5/2003 | Norlander et al. ............ 606/108 |
| 6,645,223 | B2 | * | 11/2003 | Boyle et al. ................... 606/200 |
| 6,652,568 | B1 | * | 11/2003 | Becker et al. ................. 623/1.11 |
| 7,226,440 | B2 | * | 6/2007 | Gelfand et al. ............... 604/509 |
| 2004/0215139 | A1 | * | 10/2004 | Cohen ......................... 604/95.04 |
| 2005/0181004 | A1 | * | 8/2005 | Hunter et al. ................. 424/422 |

OTHER PUBLICATIONS

Ramza et al. "Safety and Effectiveness of Placement of Pacemaker and Defibrillator Leads in the Axillary Vein Guided by Contrast Venography". Am J Cardiol 1997;80:892-896.*

* cited by examiner

*Primary Examiner* — Unsu Jung
*Assistant Examiner* — Phong K Huynh
(74) *Attorney, Agent, or Firm* — Convergence Intellectual Property Law P.C.; Steven Gong; D. Bommi Bommannan (57) ABSTRACT

Medical devices, systems and methods for providing visualization as well as support and/or stability for blood vessels during procedures for inserting electrical leads are disclosed. One aspect of the device may include a longitudinal member having a distal end and a proximal end, an expandable element near the distal end of the longitudinal member for providing support to the blood vessel, and a contrast release port near the distal end of the longitudinal member for releasing a contrast medium into the blood vessel to visualize the blood vessel.

20 Claims, 12 Drawing Sheets

METHOD AND DEVICE FOR INSERTING ELECTRICAL LEADS

CROSS REFERENCE TO RELATED APPLICATIONS

This application claims priority to U.S. Provisional Patent Application No. 61/094,374, titled "Method and Device for Inserting Electrical Leads" and filed on Sep. 4, 2008.

FIELD OF THE INVENTION

This invention relates generally to catheters, and in particular to a catheter device for providing visualization and support to the subclavian vein for the delivery of electrical leads to the heart.

DESCRIPTION OF THE RELATED ART

The invention relates to the field of cardiology and in particular to methods and devices for inserting pacemaker or implantable cardioverter defibrillator (ICD) leads.

A pacemaker is typically composed of three parts: a pulse generator, one or more leads, and an electrode on each lead. The pulse generator is a small metal case that contains electronic circuitry that regulates the impulses sent to the heart. The leads are insulated wires that are connected at one end to the pulse generator and on the other end to the inside of the heart. The electrodes on the leads are in contact with the heart wall.

The leads are percutaneously inserted into a blood vessel, typically the subclavian vein, with the aid of a sheath or introducer. The leads are advanced through the sheath into the blood vessel and to the heart.

A problem often encountered during this procedure is readily accessing the blood vessel so that the leads can be delivered to their intended site. At times, access can be so difficult and time consuming that it may cause the physician to abandon the procedure and reattempt at another time. In addition, properly locating the puncture site for lead insertion is important so as to prevent any potential damage to the underlying tissues or organs. These problems are typically caused by the fact that the target vessel cannot be visualized from outside the body, lacks stability, and is prone to collapsing.

Therefore, it is desirable to provide a device which can prepare the target blood vessel for effective and safe delivery of the leads.

SUMMARY OF THE INVENTION

A catheter device for providing visualization as well as support and/or stability for blood vessels during procedures for inserting electrical leads. In one particular aspect, the catheter device is used when inserting pacemaker or ICD leads through the subclavian blood vessel.

In one aspect, the catheter device comprises a longitudinal member having a distal end and a proximal end, an expandable element near the distal end of the longitudinal member for providing support to the blood vessel, and a contrast release port near the distal end of the longitudinal member for releasing a contrast medium into the blood vessel to visualize the blood vessel. At its proximal end, the catheter device comprises a contrast injection port.

In various aspects, the expandable element may comprise an inflatable balloon, or a plurality of compressible elements that expand to a balloon like shape, or a compressible coil housed in a protective sheath, which sheath retracts to allow the coil to expand. In one aspect, the catheter device comprises two inflatable balloons. At its proximal end, the catheter device comprises one or more inflation ports for inflating the one or more balloons.

As part of a surgical procedure to insert an electrical lead into the subclavian vein of a patient and from there into the heart, a physician first advances the catheter device into the subclavian vein and then causes the expandable member to expand and thereby to support the blood vessel. The physician then releases a contrast medium through the contrast release port into the blood vessel to visualize the blood vessel. Finally, the physician inserts a hollow point needle into the visualized and supported subclavian vein, and then proceeds to insert the electrical lead through the needle and into the subclavian vein. From there the physician navigates the lead into the patient's heart.

BRIEF DESCRIPTION OF THE DRAWINGS

The invention has other advantages and features which will be more readily apparent from the following detailed description of the invention and the appended claims, when taken in conjunction with the accompanying drawings, in which:

DETAILED DESCRIPTION OF THE PREFERRED EMBODIMENTS

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as described here.

The catheter device of the present invention is provided for the visualization and support of blood vessels during surgical procedures for inserting electrical leads into blood vessels. One particular use of such a catheter device is for safer and easier insertion of pacemaker or ICD leads through the subclavian blood vessel.

In one embodiment, the catheter device comprises two balloons at its distal end which are separated along the length of the catheter device by a small distance. Once the catheter device is inserted into a blood vessel, the balloons are inflated to provide support and/or stability to the portion of the blood vessel that extends between the balloons. The catheter device comprises a port in the space between the balloons for releasing a contrast medium for visualizing the vessel. The contrast medium is injected proximally into the catheter device and travels through the catheter in a distal direction until it flows out of the port between the balloons and into the supported portion of the blood vessel, thereby allowing visualization of the blood vessel. The balloons can be of any number of materials, including but not limited to latex, nylons, PEBAX, polyurethane, polyethylene terephthalate (PET), and silicone.

Figure 1:
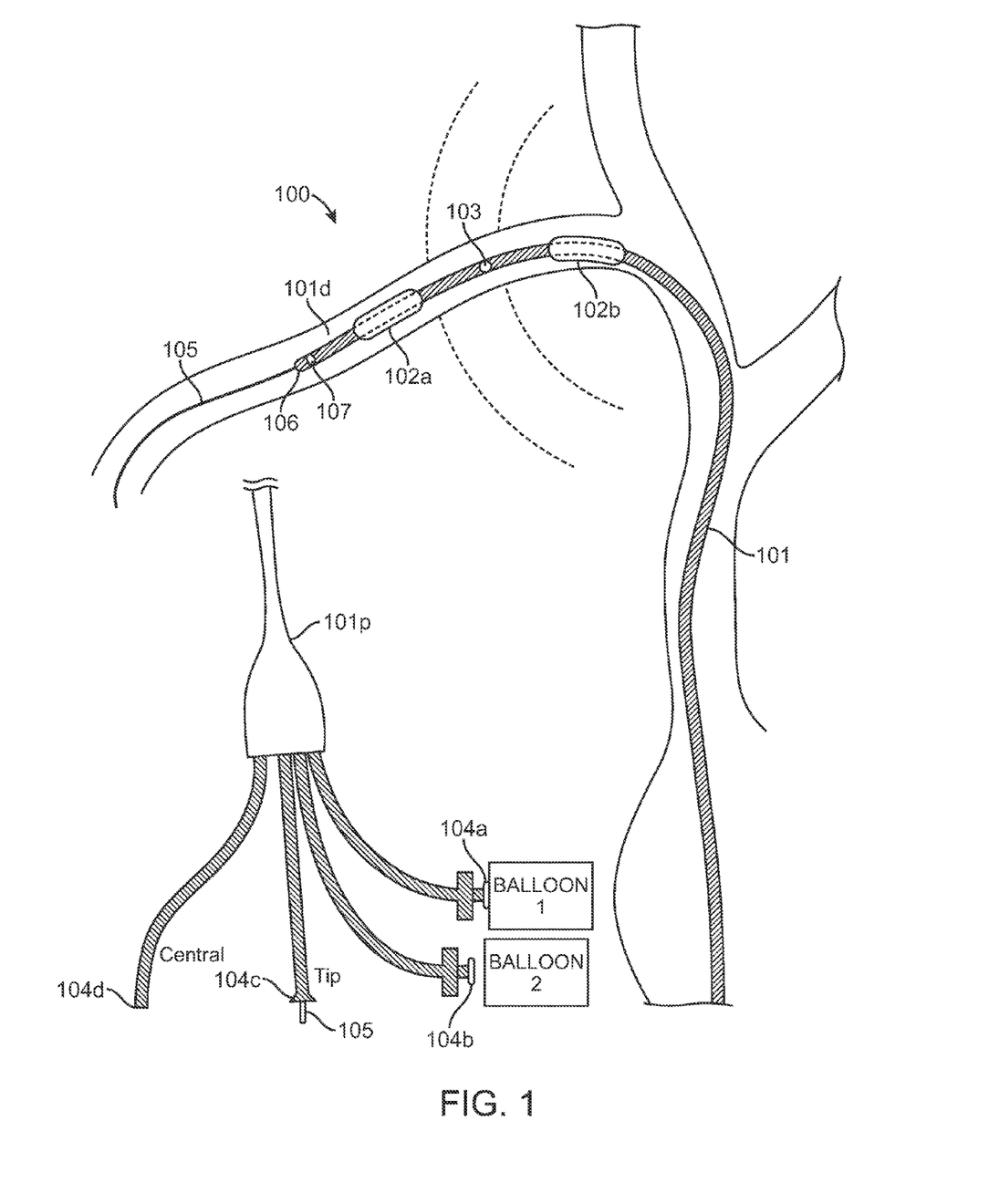
FIG. 1 illustrates one embodiment of the catheter device of the present invention.

FIG. 1 illustrates one embodiment of the catheter device. Catheter device 100 comprises a longitudinal member 101 with a distal end 101d and a proximal end 101p. The distal end 101d comprises two inflatable balloons 102a and 102b separated by a space. The catheter device 100 comprises a release port 103 in the space between the balloons 102a and 102b for delivering a contrast medium into the portion of the blood vessel supported by the balloons.

At its proximal end 101p, the catheter device 100 comprises two inflation ports 104a and 104b, a guidewire port 104c, and a contrast injection port 104d. The inflation ports 104a and 104b serve to inflate the balloons 102a and 102b, respectively. The guidewire port 104c accepts a guidewire 105. The contrast injection port 104d is configured to accept injection of a contrast medium, to be delivered through the longitudinal member 101 and out of the contrast release port 103 into the supported portion of the blood vessel. In one embodiment, the catheter device 100 comprises an atraumatic tip 106. Optionally, catheter device 100 comprises one or more radiopaque markers 107 placed along the distal portion of the catheter device 100 and/or around the balloons 102a and 102b.

Figure 2:
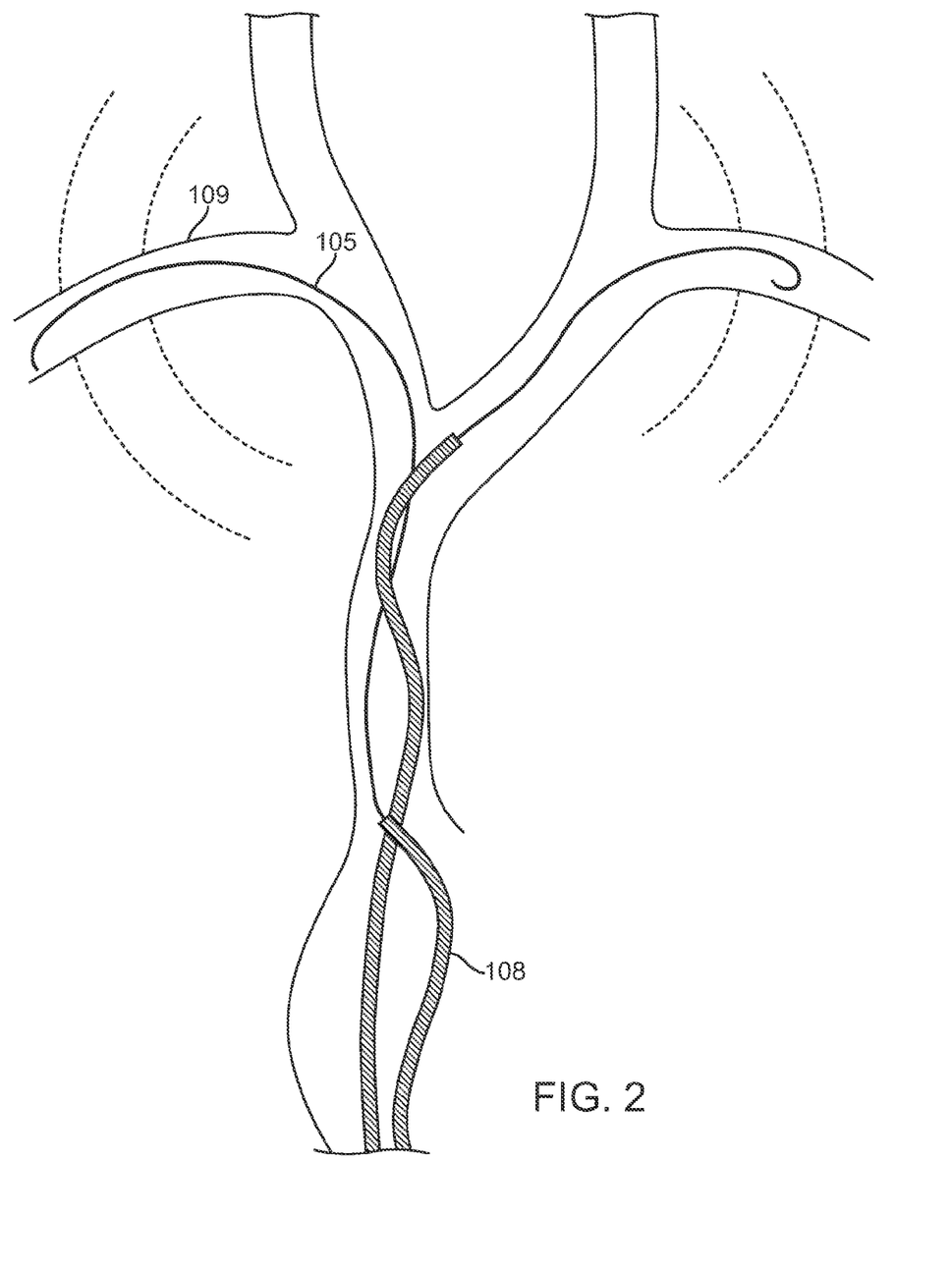
FIG. 2 illustrates two example pairs of guidewires and guiding catheters used to deliver the catheter device of the present invention into the subclavian vein.
Figure 3:
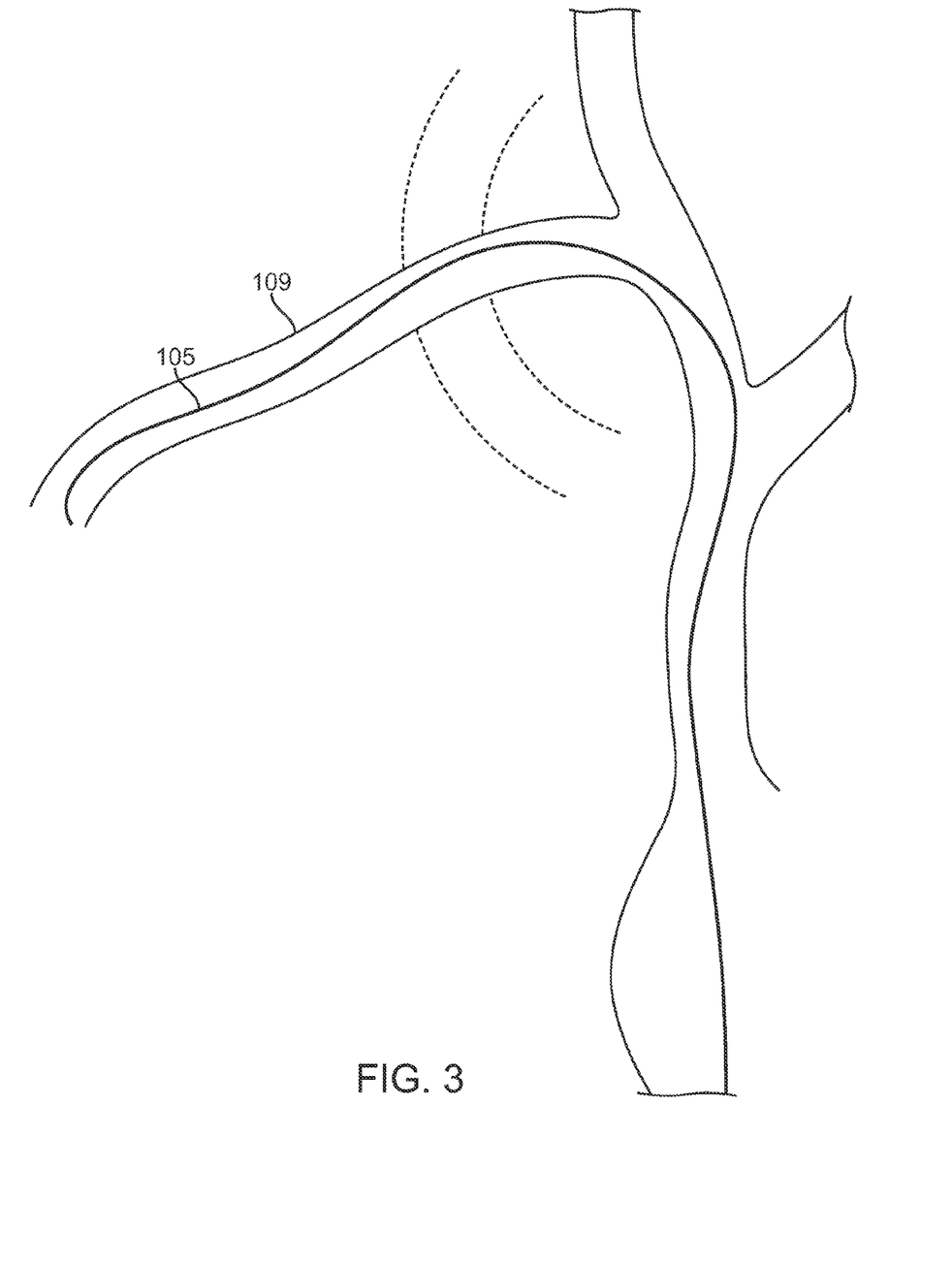
FIG. 3 shows a guidewire in place in the right subclavian vein, after removal of the corresponding guiding catheter.

As shown in FIG. 2, the guidewire 105, and typically also a guiding catheter 108, are inserted into a blood vessel to aid in the delivery of the catheter device 100. Typically, the guidewire 105 and guiding catheter 108 are introduced through the femorals or brachials, and the guiding catheter 108 is used to direct the guidewire 105 into a subclavian vein 109. It is noted that FIG. 2 actually shows two separate example pairs of a guidewire 105 and a guiding catheter 108. One pair is shown for the delivery of the guidewire 105 into the right subclavian vein 109, and the other pair is shown for delivery into the left subclavian vein. Once the guidewire 105 is in place in the subclavian vein 109, the guiding catheter 108 can be removed. FIG. 3 shows the guidewire 105 in place in the right subclavian vein 109, after removal of the guiding catheter 108. The guidewire 105 may be a standard 0.035" guidewire, or it may be of another type or dimension.

Figure 4:
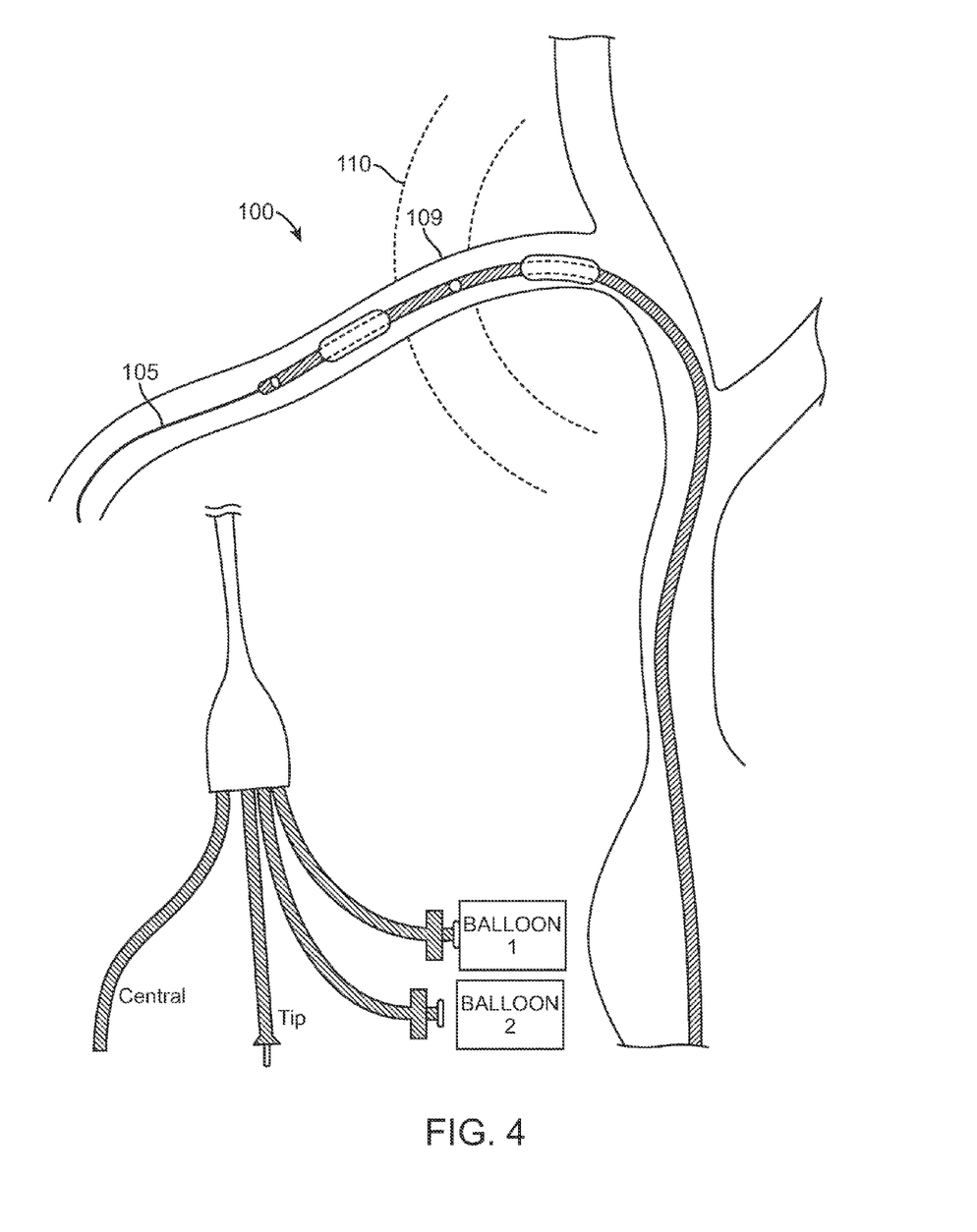
FIG. 4 shows the catheter device of the present invention tracked over the guidewire and placed in the subclavian vein.

Once the guidewire 105 is in place in the subclavian vein 109 and the guiding catheter 108 is removed, the catheter device 100 is tracked over the guidewire 105 and advanced to the subclavian vein 109 at a location just above the first rib 110, as shown in FIG. 4. This serves the purpose of one or more ribs (primarily the first rib) acting as a barrier to prevent damage to the underlying tissue when the hollow point needle is subsequently inserted as described below.

Figure 5:
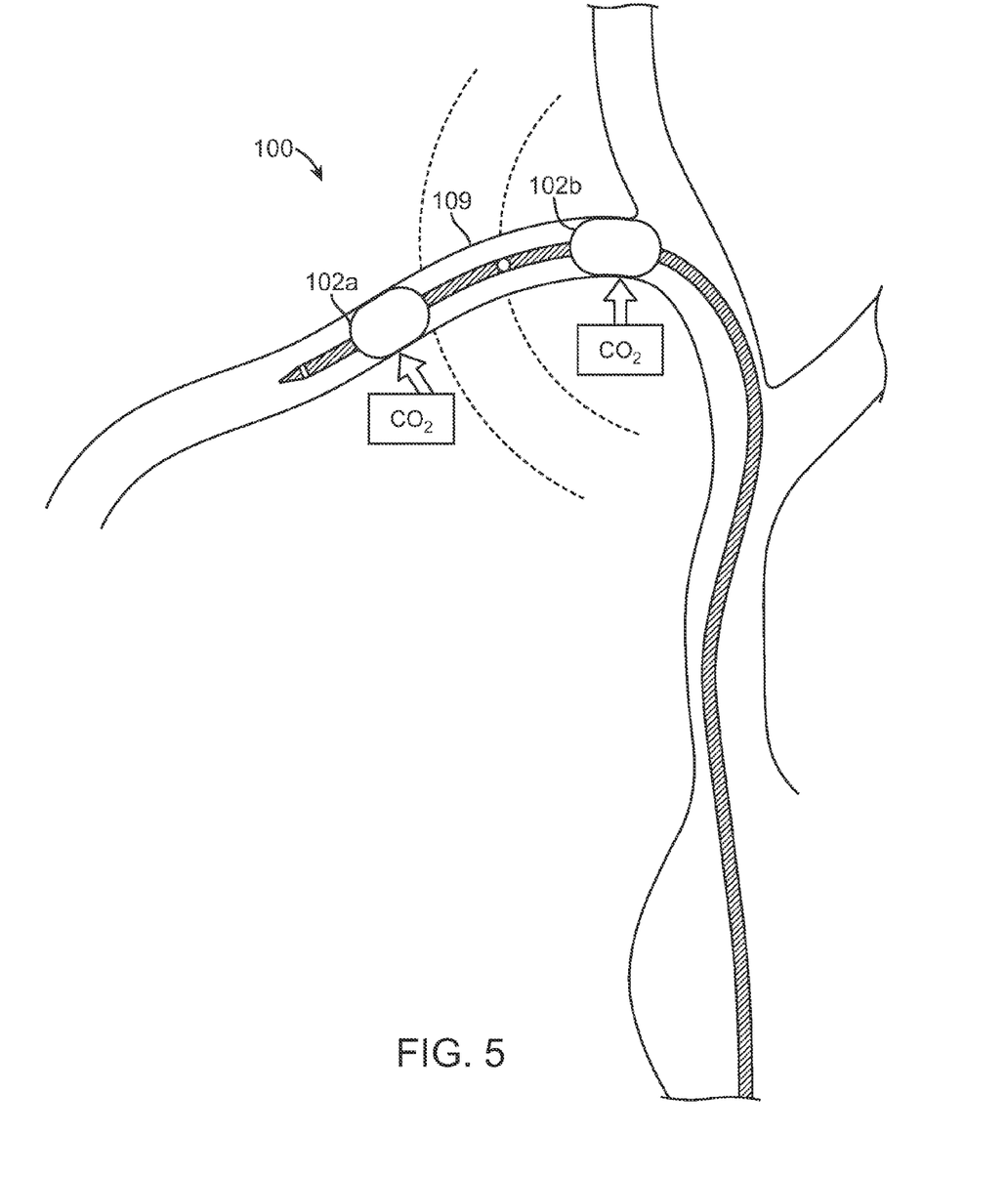
FIG. 5 shows the balloons in their inflated state.

Once the catheter device 100 is in place in the subclavian vein 109, the balloons 102a and 102b are inflated, using the inflation ports 104a and 104b at the proximal end 101p of the catheter device 100. FIG. 5 shows the balloons 102a and 102b in their inflated state. Once the balloons are inflated, they provide support and/or stability to the portion of the subclavian vein 109 that extends between the balloons, thereby reducing the vessel's tendency to collapse. The balloons 102a and 102b may be inflated using $CO_2$, saline, or any other suitable fluid.

Figure 6:
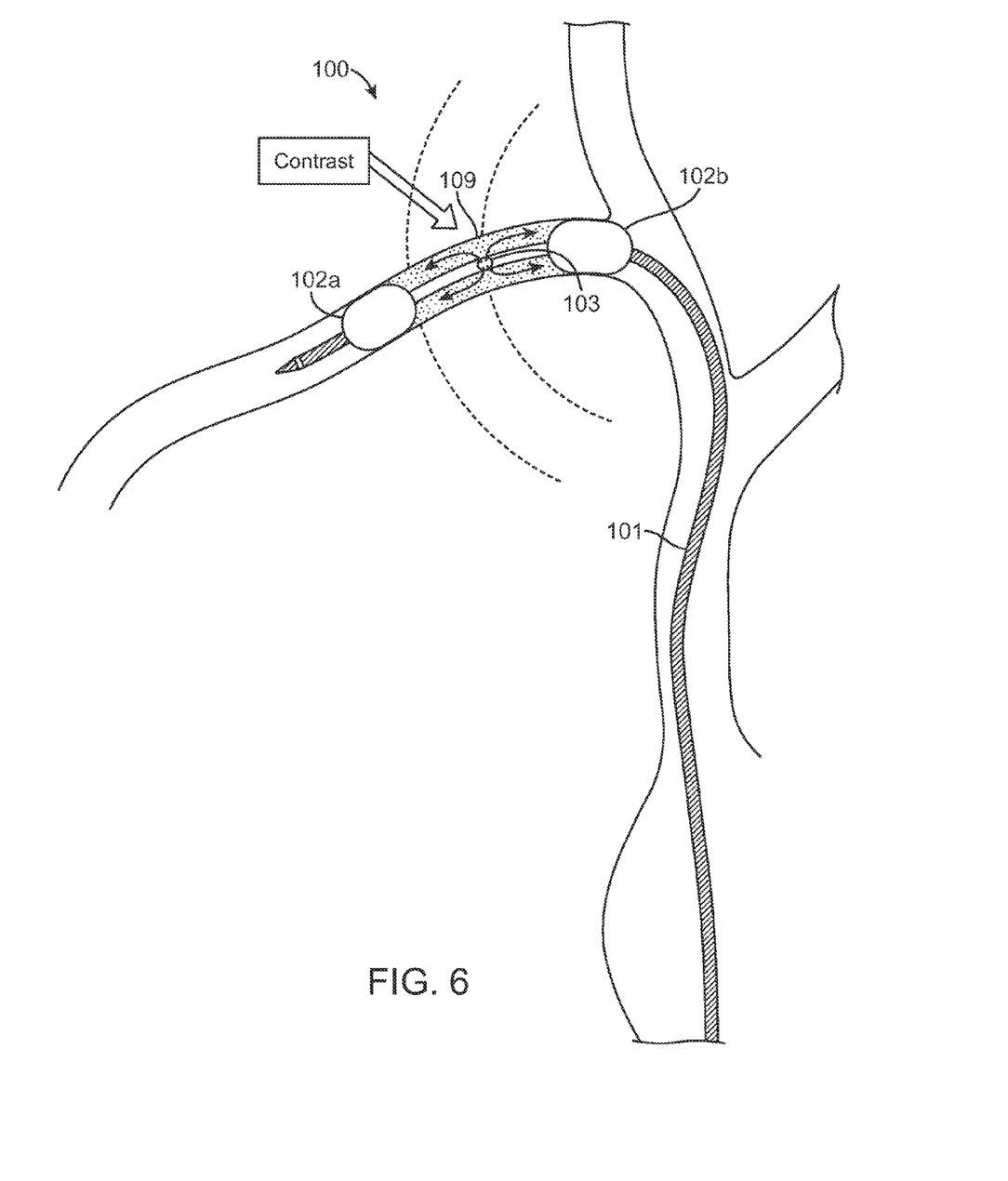
FIG. 6 shows the injection of a contrast medium into the portion of the subclavian vein that extends between and is supported by the two balloons.

Once the balloons 102a and 102b are inflated and provide support for the subclavian vein 109, a contrast medium is injected into the contrast injection port 104d at the proximal end 101p of the catheter device 100. The injected contrast medium travels in a distal direction through the longitudinal member 101 and out of the contrast release port 103 into the supported portion of the subclavian vein 109, as shown in FIG. 6. While injection of the contrast medium primarily provides for visualization, it also serves the additional purpose of dilating the subclavian vein 109 and thereby providing additional support and/or stability to the vein. Optionally, the contrast medium itself may be used to inflate the balloons 102a and 102b. Optionally, one or more of the balloons 102a and 102b comprises one or more radiopaque markers for additional aid in visualization.

Figure 7:
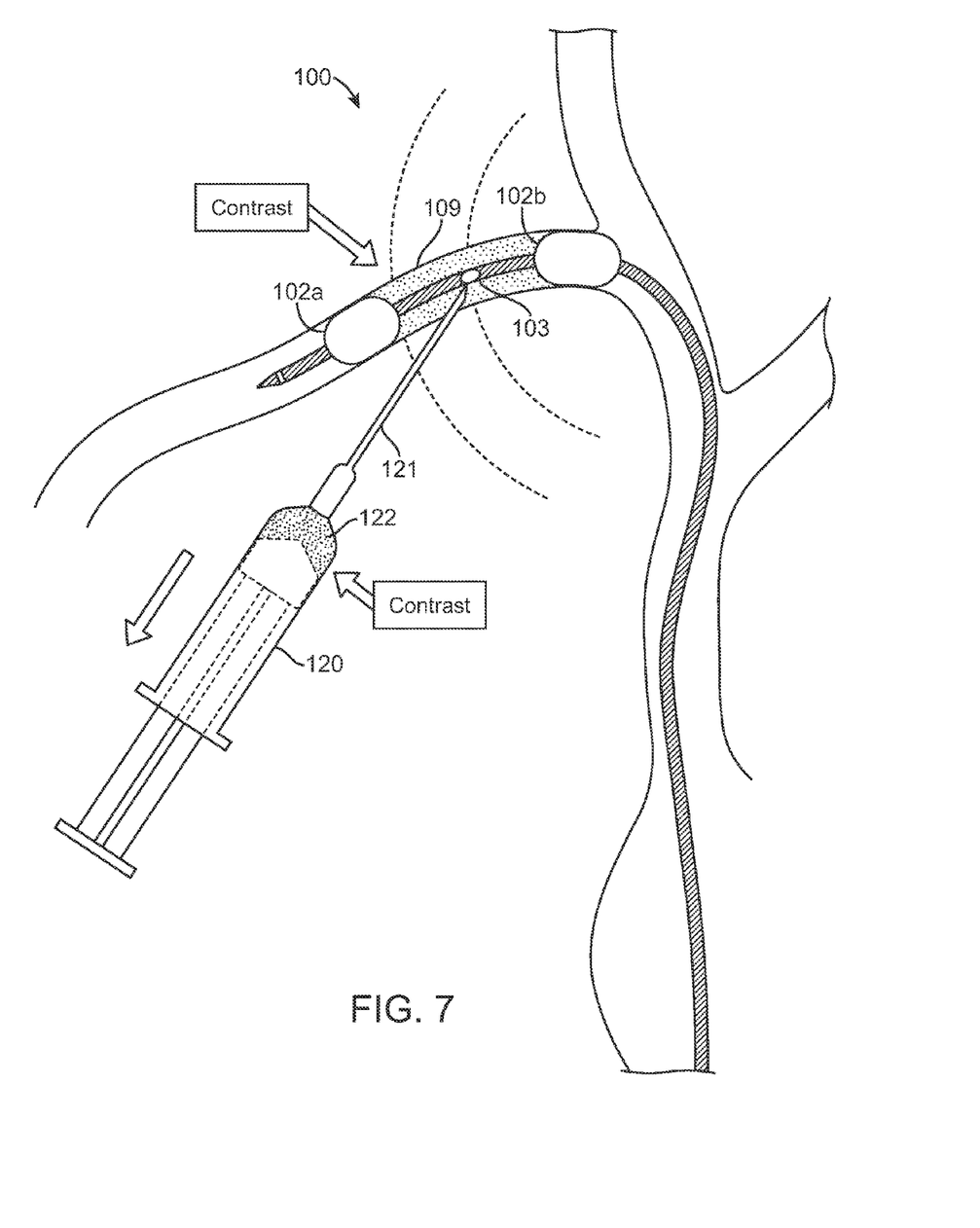
FIG. 7 illustrates a syringe and needle used to draw blood to obtain visual confirmation of the presence of the needle in the blood vessel.

With the contrast medium present in the supported portion of the subclavian vein 109, the subclavian can be easily visualized under fluoroscopy. A syringe with a hollow point needle can then be used to draw some blood from the subclavian vein 109 and, upon visual confirmation that the contrast medium is present in the drawn blood, to confirm that the needle is within the subclavian vein 109. This is shown in FIG. 7, wherein a syringe 120 with a needle 121 is used to draw a small amount of blood 122 from the subclavian vein 109 and to confirm the presence of contrast medium in the drawn blood 122.

Figure 8:
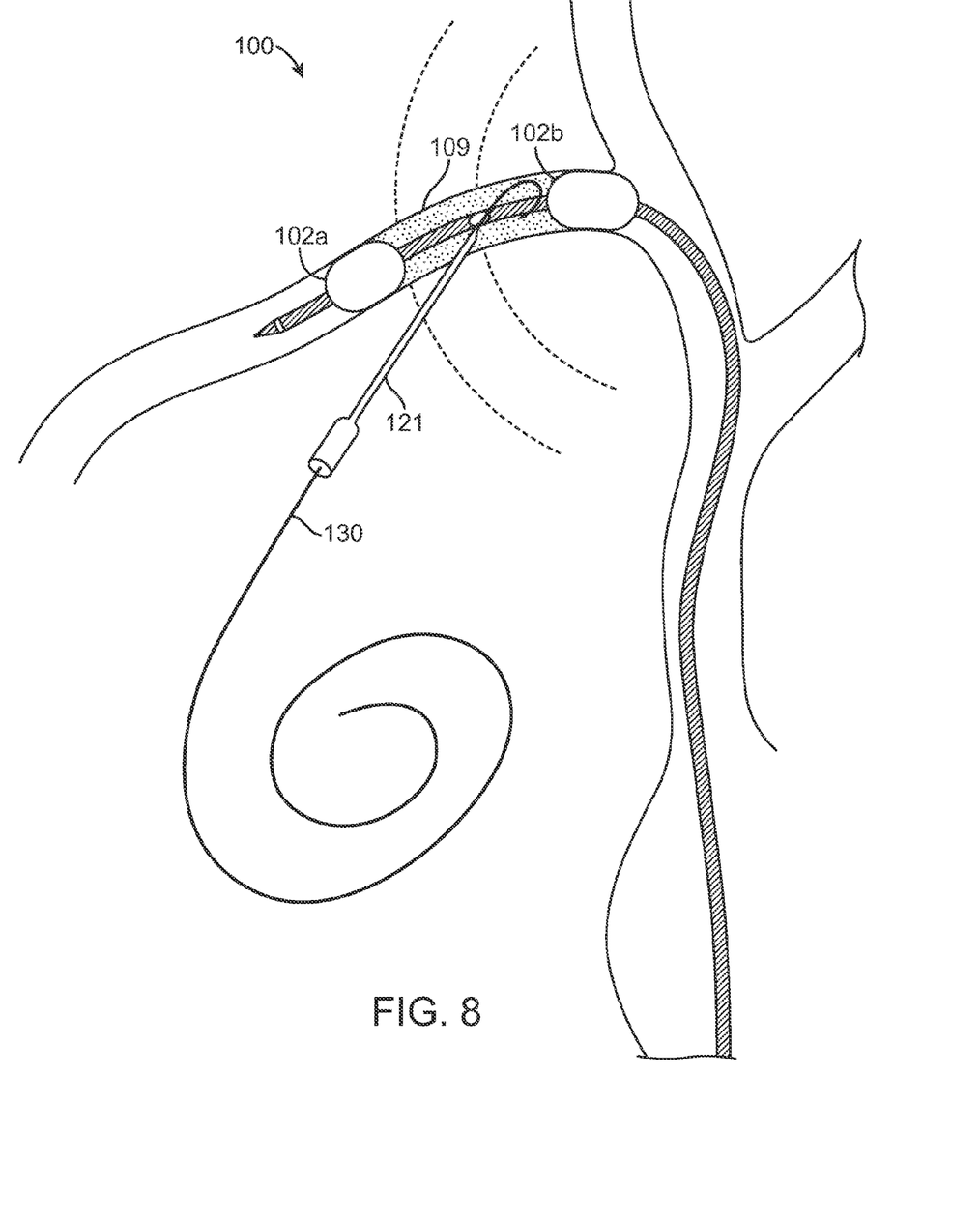
FIG. 8 illustrates the insertion of an electrical lead through the needle and into the subclavian vein.

Upon such visual confirmation of contrast presence using syringe 120 and needle 121, the syringe 120 is removed and the needle 121 is left in place in preparation for the delivery of one or more electrical leads. FIG. 8 shows insertion of an electrical lead 130 through the needle 121 and into the subclavian vein 109.

Figure 9:
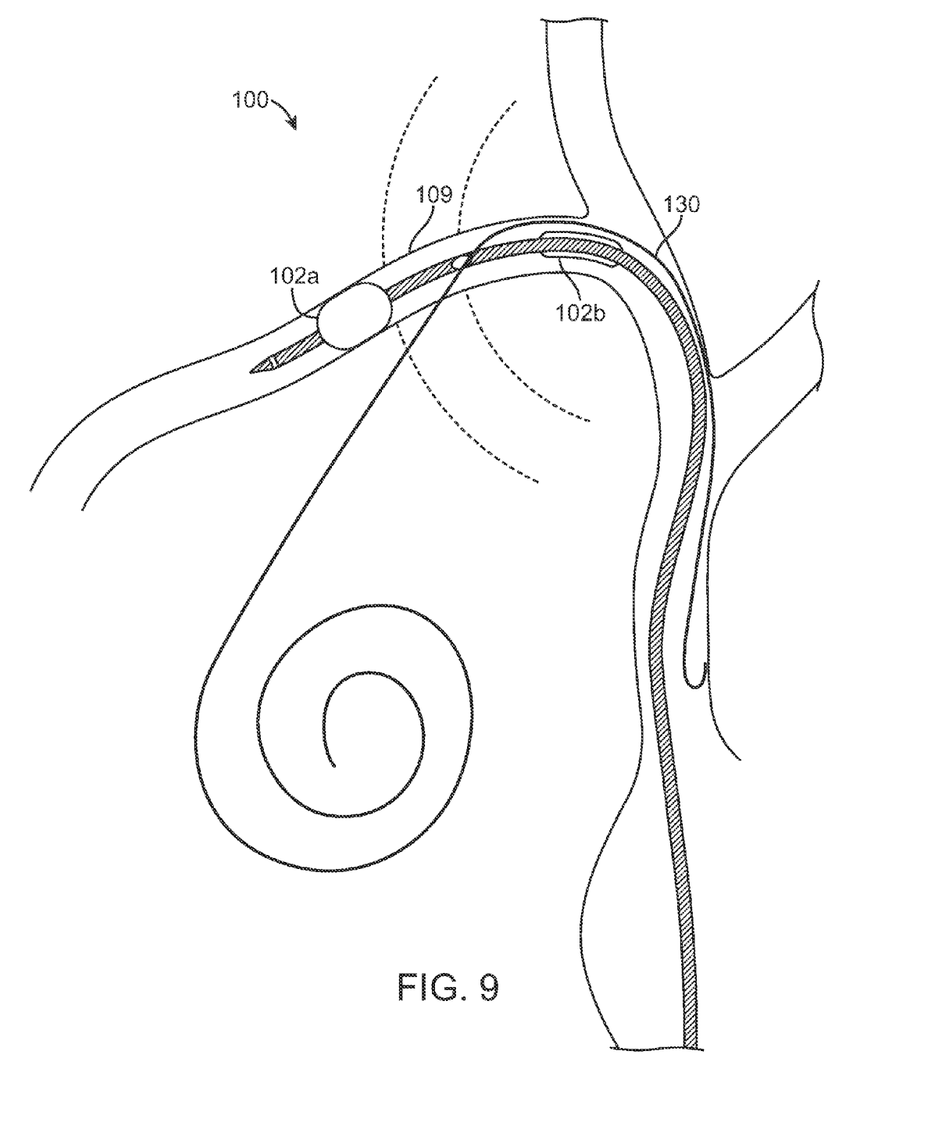
FIG. 9 shows the deflated proximal balloon and the inserted lead traveling past the deflated balloon and further down the blood vessel towards the heart.

Once the electrical lead 130 is inserted into the subclavian vein 109, the proximal balloon 102b is deflated to allow the lead 130 to be placed further down the blood vessel for delivery to its intended site in the heart. This is illustrated in FIG. 9, showing the deflated proximal balloon 102b and the lead 130 traveling past the deflated balloon 102b and further down the blood vessel towards the heart.

In an alternative embodiment, the catheter device 100 comprises one balloon 102b and one corresponding inflation port, but not another balloon nor another corresponding inflation port. Once the catheter device 100 is placed into the subclavian vein 109 as described above, the balloon 102b is inflated. Inflation of the balloon 102b causes the blood to back up distal to the inflated balloon 102b, thereby dilating and providing support and/or stability to the subclavian vein 109. Optionally, contrast medium is injected and released via the contrast release port 103 to provide visualization. The physician then proceeds with inserting the electrical leads as described above. It should be noted that the contrast release port 103 can be placed on either side of the balloon.

Figures 10, 10A:
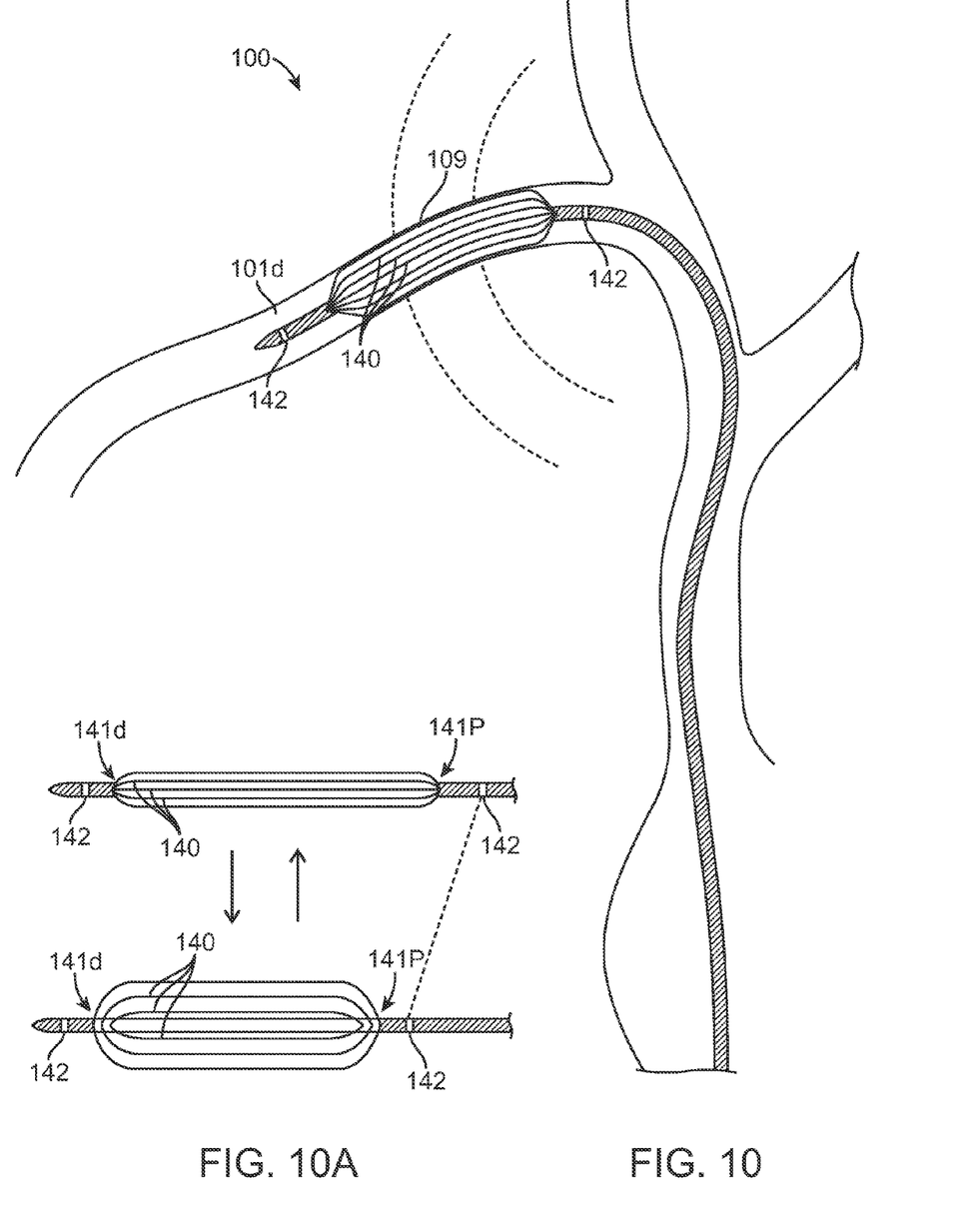
FIGS. 10-10A and 11A-11B show alternative embodiments of the catheter device comprising compressible elements.

In another alternative embodiment, the catheter device 100 does not comprise inflatable balloons, but instead comprises a number of compressible elements which can be expanded to take a shape similar to a balloon. FIG. 10 shows such an embodiment, wherein catheter device 100 comprises compressible elements 140 which extend axially along the distal end of the catheter device 100. Upon activation, and as shown in FIG. 10A, the elements 140 expand to take a shape similar to a balloon, thereby providing support and/or stability to the portion of the subclavian vein 109 within which the elements 140 reside. The space between elements 140 allows the physician access to the heart without having to remove, compress, or otherwise handle the elements 140. The elements 140 may be activated to expand via a variety of mechanisms, including but not limited to advancing the proximal end 141*p* of the compressible elements 140 towards the distal end 141*d*, or vice versa. This may be accomplished by pulling on the distal end 141*d* to cause it to move towards the proximal end 141*p*, or by twisting or rotating the proximal end 141*p* relative to the distal end 141*d* in order to cause the elements 140 to expand outwards, or by similar techniques. Optionally, the elements 140 are radiopaque to allow visualization of the blood vessel 109. Optionally, the distal portion of the catheter 100 comprises one or more radiopaque markers 142.

Figure 11A:
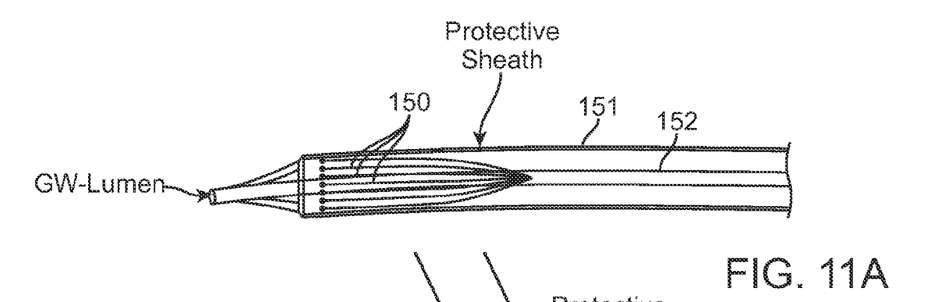
Figure 11B:
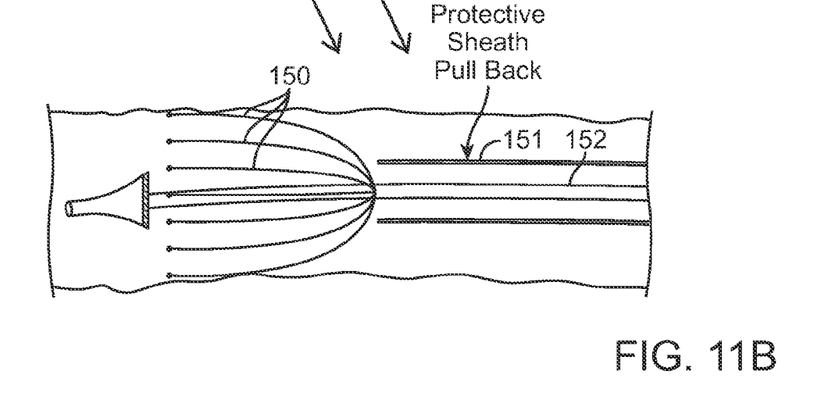

In yet another embodiment, as shown in FIG. 11A, the catheter device 100 comprises a number of compressible elements 150 housed within a protective sheath 151. The elements 150 may be affixed to a shaft 152 at their proximal end and are open at their distal end, allowing them to expand as the sheath 151 is retracted in a proximal direction. FIG. 11B shows the sheath 151 retracted and the compressible elements 150 expanded to their natural shape, thereby providing support and/or stability for the subclavian vein 109. As with the previous embodiment, the space between the elements 150 allows the physician access to the heart without having to remove, compress, or otherwise handle the elements 150. In one embodiment, shaft 152 may be a guidewire shaft comprising a guidewire lumen for a guidewire to travel through. Optionally, the elements 150 are radiopaque to allow visualization of the blood vessel 109. Optionally, the distal portion of the catheter 100 comprises one of more radiopaque markers.

Figure 12A:
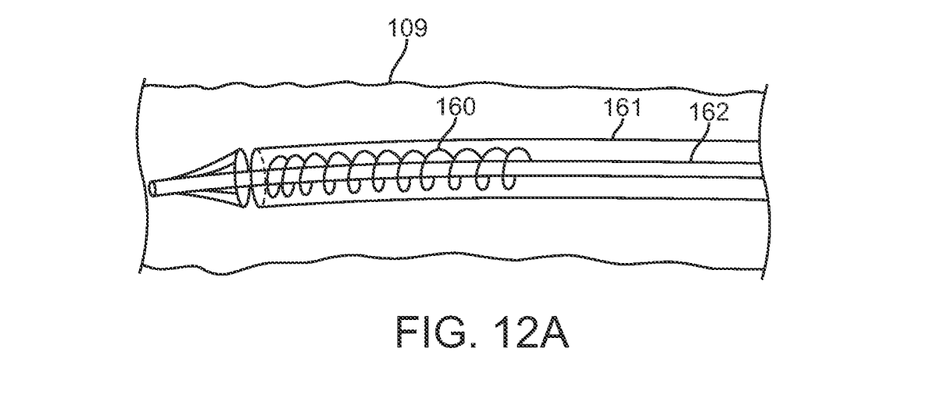
FIGS. 12A-12B show an alternative embodiment of the catheter device comprising a compressible coil.
Figure 12B:
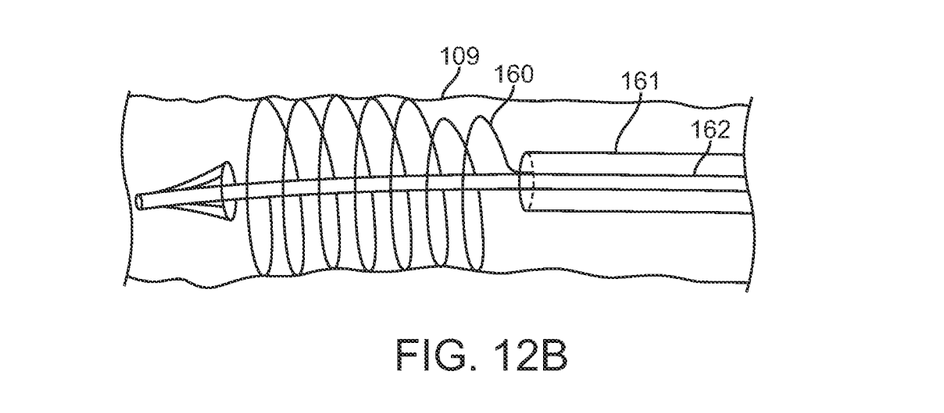

In yet another embodiment, as shown in FIG. 12A, the catheter device 100 comprises a coil 160 to provide visualization and support. The coil 160 is held in its compressed state via a number of mechanisms, including but not limited to using a protective sheath 161, tension wires (not shown), or other mechanisms. The coil 160 may be affixed to a shaft 162 at its proximal end and is open at its distal end, allowing it to expand as the sheath 161 is retracted in a proximal direction, as shown in FIG. 12B. Once the physician has inserted one or more electrical leads into the blood vessel, the coil 160 may be retracted to allow the physician unencumbered access to the heart. In one embodiment, shaft 162 may be a guidewire shaft comprising a guidewire lumen for a guidewire to travel through. Optionally, the coil 160 is radiopaque to allow visualization of the blood vessel 109. Optionally, the distal portion of the catheter 100 comprises one or more radiopaque markers.

In yet another embodiment, the catheter device 100 comprises an inflatable balloon on its distal end. After the balloon is advanced to its intended site, it is inflated with a contrast solution to provide both visualization and support. A hollow needle is then inserted through the skin and into the balloon, essentially puncturing the balloon and confirming placement of the needle inside the vessel. The balloon is then deflated and removed and the electrical leads are inserted through the needle and advanced towards the heart as described previously.

The compressible members and coils in the above embodiments may comprise a shape memory material such as Nitinol or other materials which can serve its intended purpose.

While the above embodiments generally refer to the subclavian vein as the blood vessel being visualized and supported and/or stabilized, it is understood that the catheter device of the present embodiments can be used to visualize and provide support and/or stability to other blood vessels as well. Depending on the access site chosen (femoral, brachial, radial, etc.), the location or orientation of the balloons, compressible elements, coil, contrast release port, etc. may need to be modified to serve their intended purposes.

While the above description generally makes reference to electrical leads, the device can be applicable to other non-electrical leads, catheters, or wires which may benefit from a stabilized vessel for insertion.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for locating an electrical lead insertion site and inserting electrical leads into a blood vessel, comprising:
   inserting a catheter device with a proximal and a distal end into a blood vessel, the catheter device comprising a first expandable member, a second expandable member distal to the first expandable member and a contrast release port disposed between the first and the second expandable member near the distal end;
   expanding the first expandable member and the second expandable member to create a supported region in the blood vessel;
   identifying an electrical lead insertion site at the supported region in the blood vessel between the two expandable members by releasing a contrast medium through the contrast release port to the supported region and visualizing the contrast medium in the supported region;
   inserting an electrical lead into the insertion site from an exterior of the blood vessel, wherein the insertion site is supported by the two expandable members;
   collapsing one of the expandable members while maintaining the other expandable member in an expanded state to support the blood vessel and
   traversing the electrical lead from the insertion site past the deflated expandable member to a site in the heart.

2. The method of claim 1, wherein the first expandable member comprises a first inflatable balloon, and wherein the expanding the first expandable member comprises inflating the first inflatable balloon.

3. The method of claim 1, wherein the second expandable member comprises a second inflatable balloon, and wherein the expanding the second expandable member comprises inflating the second inflatable balloon.

4. The method of claim 1, wherein at least one of the expandable members comprises a plurality of compressible elements housed within a protective sheath, and wherein the expanding comprises retracting the protective sheath, thereby allowing the plurality of compressible elements to expand outwards and provide support to the blood vessel.

5. The method of claim 1, wherein at least one of the expandable members comprises a compressible coil housed within a protective sheath, and wherein the expanding comprises retracting the protective sheath, thereby allowing the compressible coil to expand outwards and provide support to the blood vessel.

6. The method of claim 1, wherein the inserting comprises advancing the catheter to a subclavian vein at a location above the first rib thereby allowing the rib to serve as a barrier that prevents the needle from damaging underlying tissue.

7. A method for inserting electrical leads into a blood vessel, comprising:
  inserting a catheter device with a proximal and a distal end into a blood vessel, the catheter device comprising a first expandable member, a second expandable member distal to the first expandable member and a contrast release port disposed between the first and the second expandable member near the distal end; wherein at least one of the expandable members comprises one or more radiopaque markers;
  expanding the first expandable member and the second expandable member to create a supported region in the blood vessel;
  identifying an electrical lead insertion site at the supported region in the blood vessel between the two expandable members by releasing a contrast medium through the contrast release port to the supported region and visualizing the contrast medium in the supported region;
  inserting an electrical lead into the insertion site from an exterior of the blood vessel, wherein the insertion site is supported by the two expandable members;
  collapsing one of the expandable members while maintaining the other expandable member in an expanded state to prevent the blood vessel from collapsing, and
  traversing the electrical lead from the insertion site past the deflated expandable member to a site in the heart.

8. The method of claim 1, wherein the identifying comprises drawing blood from the supported region using a syringe and needle.

9. The method of claim 1, wherein the inserting comprises delivering the electrical lead using a syringe and needle.

10. A method for stabilizing a blood vessel for inserting electrical leads into the blood vessel, comprising:
  inserting a catheter device with a proximal and a distal end into the blood vessel, the catheter device comprising at least one stabilizing member;
  stabilizing a region of the blood vessel by activating the stabilizing member such that movement of the region of the blood vessel is reduced;
  inserting an electrical lead from an exterior of the blood vessel into a lead insertion site within the stabilized region of the blood vessel while maintaining the activated state of the stabilizing member; and
  traversing the electrical lead from the lead insertion site past the stabilizing member to a site in the heart.

11. The method of claim 10, wherein the stabilizing member comprises a balloon and activating the stabilizing member comprises expanding the balloon.

12. The method of claim 10, wherein the stabilizing member comprises a plurality of compressible elements housed within a protective sheath.

13. The method of claim 12, wherein activating the stabilizing member comprises retracting the sheath and expanding the plurality of compressible elements outwardly thereby providing stabilization to the region of the blood vessel.

14. The method of claim 10, wherein the stabilizing member comprises a compressible coil housed within a protective sheath.

15. The method of claim 14, wherein activating of the stabilizing member comprises retracting the sheath and expanding the compressible coil outwardly thereby providing stabilization to the region of the blood vessel.

16. The method of claim 10, further comprising occluding blood flow using the stabilizing member to dilate and stabilize the blood vessel.

17. The method of claim 10, further comprising visualizing the stabilized region of the blood vessel by releasing contrast via a contrast release port disposed on the catheter device.

18. The method of claim 10, wherein stabilizing the region of the blood vessel further comprises activating a second stabilizing member disposed on the catheter device.

19. The method of claim 18, wherein the electrical lead is inserted into the stabilized region between the two stabilizing members.

20. The method of claim 19, wherein the traversing the electrical lead from the site of insertion further comprises deactivating one of the two stabilizing members while maintaining the activated state of the other stabilizing member to prevent the blood vessel from collapsing.

* * * * *